United States Patent [19]
Hazra et al.

[11] Patent Number: 6,008,380
[45] Date of Patent: Dec. 28, 1999

[54] (2R,3S,24S)-2,3-DIACETOXY-22,23-EPOXY-24-ETHYL-β-HOMO-7-OXA-5α-CHOLESTAN-6-ONE AND A PROCESS FOR PREPARING THE SAME

[75] Inventors: Braja Gopal Hazra; Padmakar Laxman Joshi; Tirunahari Pavan Kumar, all of Maharashtra, India

[73] Assignee: Council of Scientific & Industrial Research, New Delhi, India

[21] Appl. No.: 09/050,179

[22] Filed: Mar. 30, 1998

[51] Int. Cl.[6] .................. C07D 313/06; C07D 313/10
[52] U.S. Cl. ............................................ 549/268
[58] Field of Search ............................. 548/268

[56] References Cited

FOREIGN PATENT DOCUMENTS 1-125396  5/1989  Japan .

OTHER PUBLICATIONS

Nobuo Ikekawa et al., *Chem. Pharm. Bull.* 1982, 30, 4181–4185.
Kenji Mori et al., *Tetrahedron* 1982, 38, 2099–2109.
C. W. Shoppe et al., *J. Chem. Soc.* 1957, 3100–3107.
B.G. Hazra et al., *J. Chem. Soc. Perkin Trans. I*, 1994, 1667–1669.

*Primary Examiner*—Ba K. Trinh
*Attorney, Agent, or Firm*—Greenblum & Bernstein, P.L.C.

[57] ABSTRACT

The present invention relates to a novel compound namely (2R,3S,24S)-2,3-diacetoxy-22,23-epoxy-24-ethyl-β-homo-7-oxa-5α-cholestan-6-one and a process for the preparation thereof. The said compound is represented by the structural formula

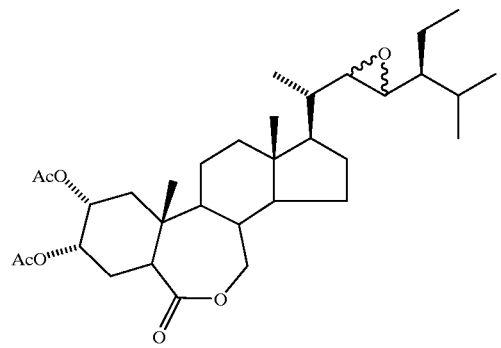

The said compound is a crucial intermediate in the synthesis of honobrassinolide having molecular formula $C_{29}H_{50}O_6$.

5 Claims, 1 Drawing Sheet

FORMULA 1

FORMULA 2

FORMULA 3

FORMULA 4

FORMULA 5

FORMULA 6

FORMULA 7

(2R,3S,24S)-2,3-DIACETOXY-22,23-EPOXY-24-ETHYL-β-HOMO-7-OXA-5α-CHOLESTAN-6-ONE AND A PROCESS FOR PREPARING THE SAME

FIELD OF THE INVENTION

This invention relates to a novel compound namely (2R,3S,24S)-2,3-diacetoxy-22,23-epoxy-24-ethyl-β-homo-7-oxa-5α-cholestan-6-one and a process for the preparing the same. The above novel compound has formula 5 as shown in the accompanying drawings and structurally represented as follows:

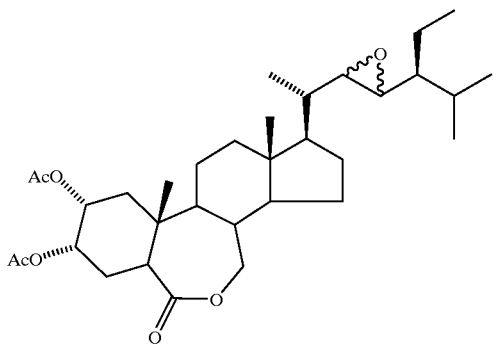

The compound of formula 5, is a crucial intermediate in the synthesis of homobrassinolide having molecular formula $C_{29}H_{50}O_6$ and isomeric structural formulae (2R,3S,22R,23R)-2,3,22,23-tetrahydroxy-24-ethyl-β-homo-7-oxa-5α-cholestan-6-one, (i.e the formula 6 as shown in the drawings) and (2R,3S,22S,23S) 24-ethyl-β-homo-7-oxa-2,3,22,23-tetrahydroxy-5α-cholestan-6-one (i.e formula 7 as shown in the drawings), both of which are highly potent plant growth promoters.

BACKGROUND OF THE INVENTION

The hitherto known processes for preparation of compound 3 are:
  (i) Oxidation of compound having formula 2 using catalytic quantity of Osmium tetroxide in the presence of N-methylmorpholine-N-oxide (Nobuo Ikekawa etal. Chem. Pharm. Bull. 1982, 30 4181–4185).
  (ii) Oxidation of compound having formula 2 with catalytic amount of Osmium tetroxide in the presence of N-methylmorpholine-N-oxide (Kenji Mori etal. Tetrahederon 1982, 38, 2099–2109).
  (iii) Oxidation of compound having formula 2 using equivalent quantity of Osmium tetroxide (C. W. Shoppe etal. J. Chem. Soc. 1957, 3100–3107).

The main drawback of all the above methods is the use of costly and highly toxic Osmium tetroxide as a reagent for the oxidation of compound having formula 2. Cis-Dihydroxylation of of said compound having formula 2 with tetradecyltrimethylammonium permanganate (TDTAP), a permanganate derived oxidizing agent, has not been reported so far. The reaction of present invention is fast, clean and can be carried out under simple condition. The reagent TDTAP is a violet crystalline solid, soluble in most of the organic solvents and easy to handle (B. G. Hazra etal. J.Chem.Soc. Perkin Trans.I 1994 1667–1669). The great advantage of the reagent TDTAP is that, it is cheap, non-toxic, selective and can be prepared very easily.

SUMMARY OF THE INVENTION

The main objective of the present invention, therefore, is to provide an environment friendly process for the preparation of the compound having formula 3 of the accompanying drawings by using alternative non-toxic reagent in place of Osmium tetroxide and suitably converting it to an important intermediate compound having formula 5 as shown in the drawings.

DETAILED DESCRIPTION OF THE INVENTION

Figure 1A:
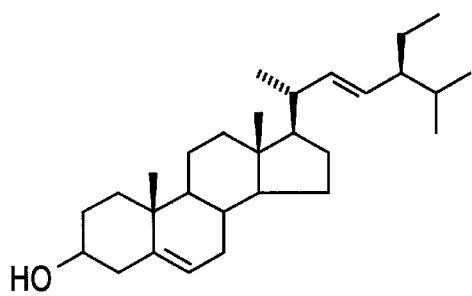
FIG. 1 presents schematic formulae 1–7 of reagents, intermediates, and products of the present invention.
Figure 1B:
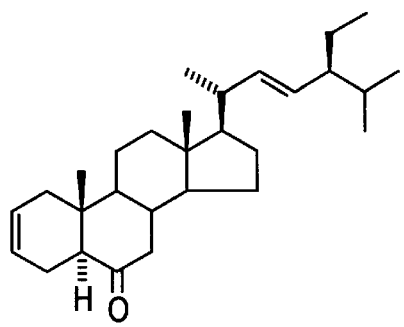
Figure 1C:
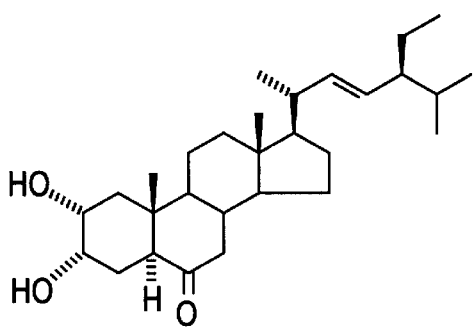
Figure 1D:
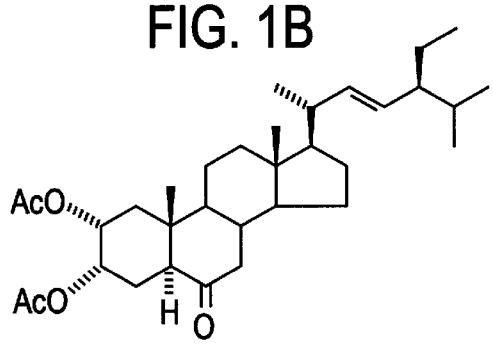
Figure 1E:
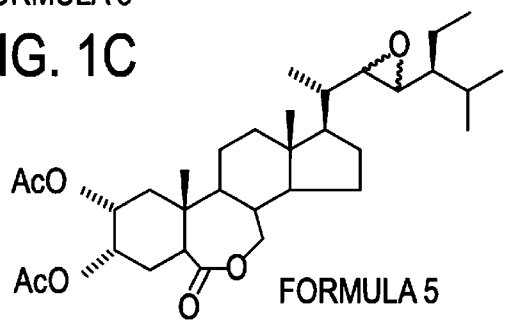
Figure 1F:
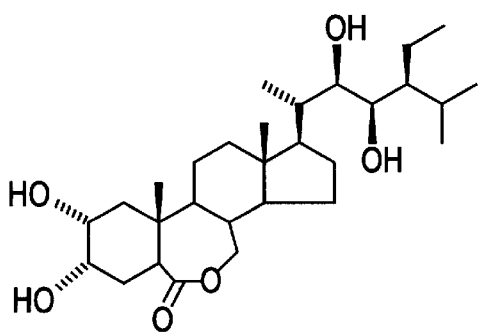
Figure 1G:
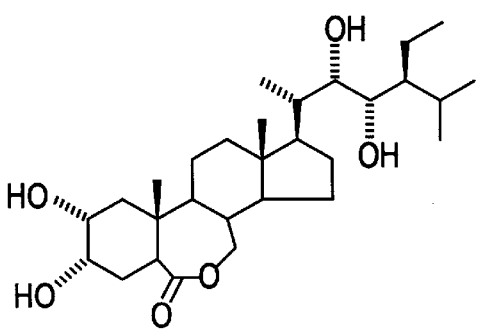

Accordingly, the present invention provides a process for the preparation of a compound represented by the following formula (5) in the accompanying drawings.

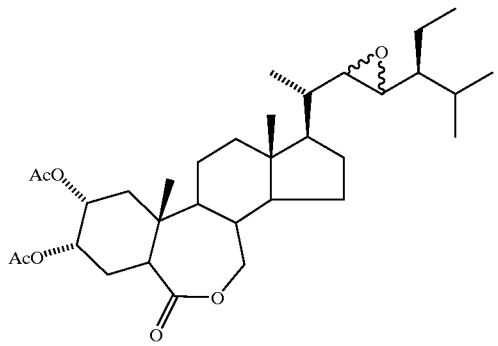

The said compound is a which is a crucial intermediate in the synthesis of homobrassinolide having molecular formula $C_{29}H_{50}O_6$ and isomeric structural formulae (2R,3S,22R,23R)-2,3,32,23-tetrahydroxy-24-ethyl-β-homo-7-oxa-5α-cholestan-6-one, which is represented by the formula (6) in the accompanying drawings.

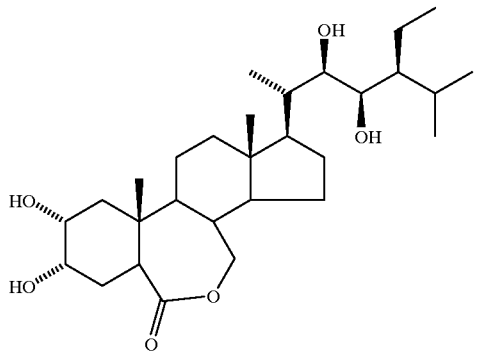

and (2R,3S,22S,23S) 24-ethyl-β-homo-7-oxa-2,3,22,23-tetrahydroxy-5α-cholestan-6-onerepresented by the formula (7) in the accompanying drawings.

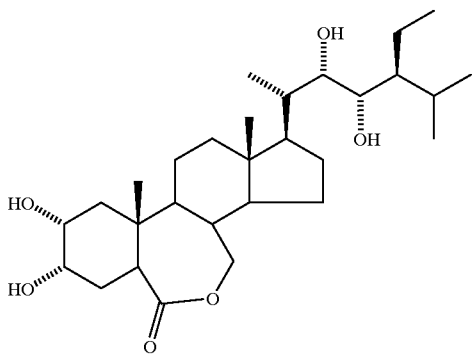

The said isomeric compounds are highly potent plant growth promoters.

The above novel compound of formula 5 is prepared from (2R,3S,22E,24S)-24-ethyl-2,3-diacetoxy-5α-cholestan-22-ene-6-one, having formula 4 as shown in the drawings, which in turn, is obtained from compound having formula 3 shown in the accompanying drawings, by acetylation. The compound having formula 3 as shown in the drawings accompanying this specification has been synthesised by dihydroxylation of (22E,24S)-24-ethyl-5α-cholestan-2,22-diene-6-one, having formula 2 as shown in the drawings accompanying this specification. Compound 2 can be obtained from stigmasterol, having formula 1 in the drawing accompanying this specification, which is chemically known as 3β-hydroxy-24-ethyl-5,22-cholestan-diene

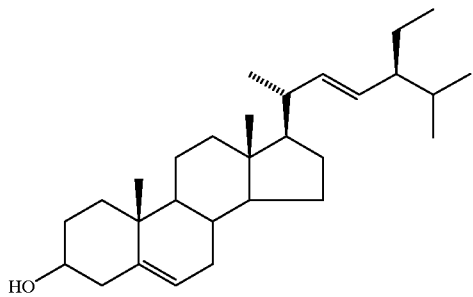

The invention further provides a process for the preparation of the above said compound (2R,3S,24S)-2,3-diacetoxy-22,23-epoxy-24-ethyl-B-homo-7-oxa-5α-cholestan-6-one, of formula 5 as shown in the drawings accompanying this specification, which comprises dihydroxylating the compound (22E,24S)-24-ethyl-5α-cholestan-2,22-diene-6-one, represented by formula 2 in the accompanying drawings in a mixture of chlorinated solvents such as methylene chloride, chloroform and tert-butanol in presence of tetradecyltrimethylammonium permanganate (TDTAP) reagent at temperature ranging from −5 to 30° C., for one to two hours and separating the resultant compound having formula 3 from the reaction mixture by column chromatography method, acetylating the compound of formula 3 to obtain compound of formula 4, oxidation of compound of formula 4 by slowly adding trifluoroperoxyacetic acid in presence of disodium hydrogen phosphate acting as a buffer at 0 to 30° C. for a period ranging between 14–18 hours to get compound of formula 5 in 67% yield and separating the said compound of formula 5 from the reaction mixture by column chromatograpy.

This oxidation of compound having formula 4 is carried out with triflouroperoxyacetic acid in presence of a phosphate buffer ($Na_2HPO_4$). Triflouroperoxyacetic acid is generated using triflouroacetic anhydride and hydrogen peroxide in methylene chloride. This solution is added slowly to a solution of compound having formula 4 in methylene chloride in presence of disodium hydrogen phosphate as a buffer at 0 to 30° C. The reaction parameters of this process have been given above.

This oxidation reaction of the compound of formula 4 with trifluroperoxyacetic acid, wherein epoxidation occirs at C-22 double bond and the Baeyer-villiger oxidation of B-ring ketone to afford a 7-membered B-ring lactone in a single step is a new one.

In an embodiment of the present invention, the trifluoroperoxyacetic acid used in the oxidation of compound of formula 4 is generated using trifluoroacetic anhydride and hydrogen peroxide in methylene chloride.

In another embodiment the chlorinated solvents used are selected from common chlorinated solvents such as methylene chloride, ethylene dichloride and chloroform.

The process of the present invention is described herein below by the following drawings examples, which are illustrative only and should not be construed to limit the scope of the present invention in any manner.

EXAMPLE 1

To a solution of (22E,24S)-24-Ethyl-5α-cholestan-2,22-diene-6-one, having formula 2 (410 mg, 1 mmol) in methylene chloride (1 ml) and tert-butanol (4 ml), benzyltrimethylammonium hydroxie (16.7 mg, 0.1 mmol) in tert-butanol (2 ml) was added. The mixture was cooled to −5° C. To this a solution of tetradecyltrimethylammonium permanganate (TDTAP) (412 mg, 1.1 mmol) in methylene chloride (3 ml) was added dropwise for a period of 10 minutes with stirring. The reaction was continued at 30° C. for a period of 2 hours. Reaction mixture was quenched with a 30% solution of $NaHSO_3$ (5 ml) and it was stirred for 15 minutes. It was filtered through a bed of celite, and the residue was washed thoroughly with dichloromethane and afterwards with water. The filtrate was evaporated and the residue was extracted with dichloromethane (3×30 ml). The organic extract was washed with water (2×30 ml), followed by saturated brine (2×30 ml) and it was dried over $Na_2SO_4$. On evaporation of the solvent a solid residue (565 mg) was obtained, which was purified by column chromatography over silica gel, furnished pure 2,3 cis-dihydroxy compound, having formula 3, 319 mg, 72% yield, m.p.233–235° C. (ethanol).

A solution of the diol (0.5 g, 1.1 mmol), $Ac_2O$ (i ml, 10.5 mmol) 4-(dimethylamino) pyridine (0.008 g, 0.06 mmol) in pyridine (2.5 ml) was stirred at 30° C. for 22 hours. It was poured on crushed ice, stirred for 1 hour and then extracted with diethyl ether. Ether extracts were successively washed with 2N HCl, water, saturated aqueous solution of $NaHCO_3$, water, saturated brine and dried. Removal of the solvent furnished a foamy solid (0.6 g) which was purified by column chromatography over silica gel (15 g) to get compound having structural formula 4 (0.58 g), 99% yield, m.p. 193–194° C. ($CH_3OH$).

A trifluoroperacetic acid solution in dichloromethane (prepared from 44% $H_2O_2$ (0.7 ml, 9.1 mmol), trifluoroacetic anhydride (2 ml, 14.14 mmol) and dicholomethane (3 ml) was added dropwise in em minutes at 0° C. to a stirred mixture of (2R,3S,22E,24S)-24-ethyl-2,3-diacetoxy-5α-cholestan-22-ene-7-one, having formula 4 (0.213 g, 0.404 mmol) in dichloromethane (19 ml) and disodium hydrogen phosphate (2.13 g, 15 mmol). The reaction was continued at this temperature for 2 hours, and at 26° C. for 15 hours. Cold water was added to the reaction mixture and dichloromethane layer was separated. Aqueous layer was extracted with dichloromethane (3×30 ml) and organic extracts were combined, washed with water (2×20 ml), saturated sodium bicarbonate solution (2×20), saturated brine (2×30 ml), and it was dried over $Na_2SO_4$. On evaporation of the solvent, a semisolid residue (208 mg) was obtained, which was purified by column chromatography over silica gel to furnish pure (2R,3S,24S)-2,3-diacetoxy-22,23-epoxy-24-ethyl-β-homo-7-oxa-5α-cholestan-6-one, of formula 5, 149.5 mg, 66% mp 118–120° C. (ethanol).

EXAMPLE 2

To a solution of (22E,24S)-24-ethyl-5α-cholestan-2,22-diene-6-one having formula 2 (615 mg, 1.5 mmol) in ethylenedichloride (2 ml) and tert-butanol (5 ml), benzyltrimethylammonium hydroxide (251 mg, 1.5 mmol) in tert-butanol (8 ml) was added. The mixture was cooled to 0° C. To this a solution of tetradecyltrimethylammonium permanganate (TDTAP) (618 mg, 1.65 mmol) in ethylene dichloride (4 ml) was added dropwise for a period of 12 minutes with stirring. The reaction was continued at 22° C. for a period of 3 hours. Reaction mixture was quenched with a 30% solution of $NaHSO_3$ (6 ml) and it was stirred for 30 minutes. It was filtered through a bed of celite, and the residue was washed thoroughly with ethylene dichloride and afterwards with water. The filtrate was evaporated and the residue was extracted with ethylenedichloride (3×30 ml). The organic extract was washed with water (2×20 ml), followed by saturated brine (2×30 ml) and it was dried over $Na_2SO_4$. On evaporation of the solvent a solid residue (740 mg) was obtained, which was purified by column chromatography over silica gel, furnished pure 2,3 cis-dihydroxy compound, having formula 3, 452 mg, 689% yield, m.p.23–235° C. (ethanol).

A solution of the diol (0.75 g, 1.6 mmol), $Ac_2O$ (2 ml, 21 mmol), 4-(dimethylamino) pyridine (0.015 g, 0.22 mmol) in pyridine (5 ml) was stirred at 30° C. for 22 hours. It was poured on crushed ice, stirred for 1 hour and then extracted with diethyl ether. Ether extracts were successively washed with 2N HCl, water, saturated aqueous solution of $NaHCO_3$, water, saturated brine and dried. Removal of the solvent furnished a foamy solid (0.9 g) which was purified by column chromatography over silica gel (20 g) to get compound having structural formula 4 (0.87 g), 99% yield, m.p. 193–194° C. ($CH_3OH$).

A trifluroperoxycetic acid solution in dicholomethane (prepared from 44% $H_2O_2$ (0.35 ml, 4.52 mmol), trifluoroacetic anhydride (1 ml, 7.07 mmol) and dicholomethane (2 ml), was added dropwise in 10 minutes at 5° C. to a stirred mixture of (2R,3S,22E,24S)-24-ethyl-2,3-diacetoxy-5α-cholestan-22-ene-6-one, of the formula 4 (0.107 g, 0.202 mmol) in dichloromethane (9.5 ml) and disodium hydrogen phosphate (1.008 g, 7.5 mmol). The reaction was continued at this temperature for 1.5 hours, and at 30° C. for 14 hours. Cold water was added to the reaction mixture and dichloromethane layer was separated. Aqueous layer was extracted with dichloromethane (3×30 ml) and organic extracts were combined, washed with water (2×22 ml), saturated sodium bicarbonate solution (2×20 ml), saturated brine (2×30 ml), and it was dried over $Na_2SO_4$. On evaporation of the solvent, a semisolid residue (123 mg) was obtained, which was purified by column chromatography over silica gel to furnish pure (2R,3S,24S)-2,3-diacetoxy-22,23-epoxy-24-ethyl-β-homo-7-oxa-5α-cholestan-6-one, of formula 5, 72 mg, 64% mp 118–120° C. (ethanol).

EXAMPLE 3

To a solution of (22E,24S)-22-ethyl-5a-cholestan-2,22-diene-6-one, having formula 2 (512 mg, 1.2 mmol) in chloroform (1.5 ml) and tert-butanol (3 ml), benzyltrimethylammonium hydroxide (20.9 mg, 0.125 mmol) in tert-butanol (3 ml) was added. The mixture was cooled to −8° C. To this a solution of tetradecyltrimethylammonium permanganate (TDTAP) (515 mg, 1.37 mmol) in chloroform (2 ml) was added dropwise for a period of 20 minutes with stirring. The reaction was continued at 32° C. for a period of 2.5 hours. Reaction mixture was quenched with a 30% solution of $NaHSO_3$ (5 ml) and it was stirred for 30 minutes. It was filtered through a bed of celite, and the residue was washed thoroughly with chloroform and afterwards with water. The filtrate was evaporated and the residue was extracted with chloroform (3×40 ml). The organic extract was washed with water (2×40 ml), followed by saturated brine (2×40 ml) and it was dried over $Na_2SO_4$. On evaporation of the solvent a solid residue (680 mg) was obtained, which was purified by column chromatography over silica gel, furnished pure 2,3 cis-dihydroxy compound having formula 3, 360 mg, 65% yield, m.p.233–235° C. (ethanol).

A solution of the diol (0.8 g, 1.76 mmol), $Ac_2O$ (2 ml, 21 mmol), 4-(dimethylamino) pyridine (0.015 g, 0.12 mmol) in pyridine (5 ml) was stirred at 30° C. for 22 hours. It was poured on crushed ice, stirred for 1 hour and then extracted with diethyl ether. Ether extracts were successively washed with 2N HCl, water, saturated aqueous solution of $NaHCO_3$, water, saturated brine and dried. Removal of the solvent furnished a foamy solid (0.96 g) which was purified by column chromatography over silica gel (2) g) to get compound having structural formula 4 (0.94 g), 99% yield, m.p.193–194° C. ($CH_3OH$).

A triflouro peracetic acid solution in dicholomethane [prepared from 45% $H_2O_2$ (1.4 ml, 18.1 mmol), triflouroacetic anhydride (4.0 ml, 28.2 mmol) and dicholomethane (6 ml)] was added dropwise in 33 minutes at 12° C. to a stirred mixture of (2R,3S,22E,24S)-24-ethyl-2,3-diacetoxy-5α-cholestan-22-ene-7-one, of the formula 4 (0.427 g, 0.808 mmol) in dichloromethane (38 ml) and disodium hydrogen phosphate (4.26 g, 30 mmol). The reaction was continued at this temperature for 3 hours and at 19° C. for 18 hours. Cold water was added to the reaction mixture and dichloromethane layer was separated. Aqueous layer was extracted with dichloromethane (3×30 ml) and organic extracts were combined, washed with water (2×20 ml), saturated sodium bicarbonate solution (2×20 ml), saturated brine (2×30 ml), and it was dried over $Na_2SO_4$. On evaporation of the solvent, a semisolid residue (470 mg) was obtained, which was purified by column chromatography over silica gel to furnish pure (2R,3S,24S)-2,3-diacetoxy-22,23-epoxy-24-ethyl-β-homo-7-oxa-5α-cholestan-6-one, of formula 5, 303 mg, 67% mp 118–120° C. (ethanol).

ADVANTAGES

The advantages of the process of the present invention are:

(a) Replacement of an expensive and highly toxic oxidizing agent Osmium tetroxide with TDTAP, which is inexpensive, very easy to handle and can be prepared easily. Cis-Dihydroxylation of compound having formula 2 with TDTAP has not been reported so far.

(b) The reaction is fast, clean and environment friendly.

(c) Reaction is selective, furnishing only 2,3 dihydroxy compound having formula 3 without affecting the C-22 double bond.

(d) one step epoxidation of the (22E)-olefin and Baeyer-Villiger oxidation of the B-ring ketone of compound having formula 4 with trifluoroperoxyaceticacetic acid furnishing a new compound having structural formula 5 is of great advantage.

We claim:

1. A process for the preparation of (2R,3S,24S)-2,3-diacetoxy-22,23-epoxy-24-ethyl-β-homo-7-oxa-5-cholestan-6-one and having the following structural formula (compound of formula 5)

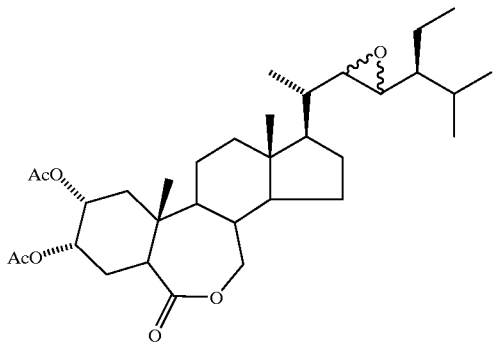

which process comprises dihydroxylating (22E,24S)-24-ethyl-5-cholestan-2,22-diene-6-one, having the following structural formula (compound of formula 2)

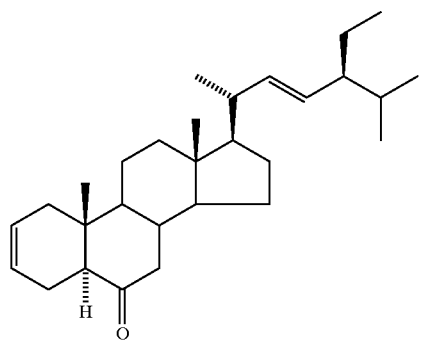

in a mixture of chlorinated solvents and in presence of tetradecyltrimethylammonium permanganate (TDTAP) reagent at temperature ranging from −5 to 30° C., for one to two hours and separating the resultant compound having the following structural formula (compound of formula 3)

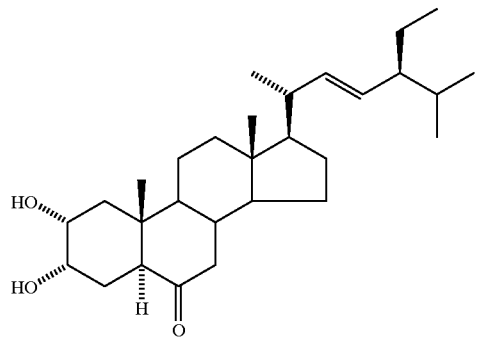

from the reaction mixture by column chromatography method, acetylating the above compound (compound of formula 3) to obtain compound of the following structural formula (compound of formula 4)

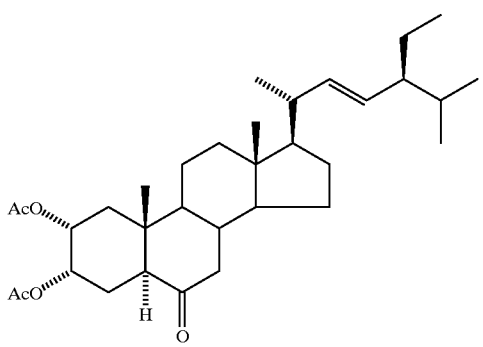

oxidation of the above compound (compound of formula 4) by slowly adding trifluoroperoxyacetic acid in presence of disodium hydrogen phosphate as a buffer at 0 to 30° C. for a period ranging between 14–18 hours to get the required compound (compound of formula 5) and separating the said compound of formula 5 from the reaction mixture by column chromatograpy.

2. The process as claimed in claim 1 wherein the trifluoroperoxyacetic acid used in the oxidation of compound of formula 4 is generated using trifluoroacetic anhydride and hydrogen peroxide in methylene chloride.

3. The process as claimed in claim 1, wherein the mixture of chlorinated solvents includes at least one of methylene chloride, ethylene dichloride, and chloroform.

4. The process as claimed in claim 1 wherein the compound having formula 2 is prepared from stigmasterol having formula 1.

5. The process as claimed in claim 1 wherein the compound of formula 5 is obtained in 67% yield.

* * * * *